United States Patent [19]
Majewski et al.

[11] Patent Number: 5,568,532
[45] Date of Patent: Oct. 22, 1996

[54] EXAMINATION SYSTEM UTILIZING IONIZING RADIATION AND A FLEXIBLE, MINIATURE RADIATION DETECTOR PROBE

[75] Inventors: Stanislaw Majewski, Grafton; Brian J. Kross; Carl J. Zorn, both of Yorktown; Lukasz A. Majewski, Grafton, all of Va.

[73] Assignee: Southeastern Universities Research Association, Inc., Newport News, Va.

[21] Appl. No.: 289,918

[22] Filed: Aug. 12, 1994

[51] Int. Cl.[6] .................................................. H05G 1/64
[52] U.S. Cl. ........................................ 378/98.3; 378/98.6
[58] Field of Search ...................................... 378/98.6, 98.3

[56] References Cited

U.S. PATENT DOCUMENTS

| | | | |
|---|---|---|---|
| 3,622,785 | 11/1971 | Irwin | 378/98.3 |
| 4,045,119 | 8/1977 | Eastgate | 385/125 |
| 4,259,583 | 3/1981 | Albert | 378/98.6 |
| 5,134,293 | 7/1992 | Anderson et al. | 250/361 |
| 5,452,395 | 9/1995 | Schichman et al. | 385/125 |

*Primary Examiner*—Craig E. Church

[57] ABSTRACT

An optimized examination system and method based on the Reverse Geometry X-Ray® (RGX®) radiography technique are presented. The examination system comprises a radiation source, at least one flexible, miniature radiation detector probe positioned in appropriate proximity to the object to be examined and to the radiation source with the object located between the source and the probe, a photodetector device attachable to an end of the miniature radiation probe, and a control unit integrated with a display device connected to the photodetector device. The miniature radiation detector probe comprises a scintillation element, a flexible light guide having a first end optically coupled to the scintillation element and having a second end attachable to the photodetector device, and an opaque, environmentally-resistant sheath surrounding the flexible light guide. The probe may be portable and insertable, or may be fixed in place within the object to be examined. An enclosed, flexible, liquid light guide is also presented, which comprises a thin-walled flexible tube, a liquid, preferably mineral oil, contained within the tube, a scintillation element located at a first end of the tube, closures located at both ends of the tube, and an opaque, environmentally-resistant sheath surrounding the flexible tube. The examination system and method have applications in non-destructive material testing for voids, cracks, and corrosion, and may be used in areas containing hazardous materials. In addition, the system and method have applications for medical and dental imaging.

8 Claims, 4 Drawing Sheets

EXAMINATION SYSTEM UTILIZING IONIZING RADIATION AND A FLEXIBLE, MINIATURE RADIATION DETECTOR PROBE

The United States may have certain rights to this invention, under Management and Operating Contract DE-AC05-84ER40150 from the United States Department of Energy.

BACKGROUND OF THE INVENTION

1. Field of the Invention

The present invention relates to radiography and more particularly to an examination system and method utilizing ionizing radiation and a flexible, miniature radiation detector probe.

2. Description of the Related Art

X-radiography is useful in many areas of non-destructive testing especially when voids, cracks, and corrosion in assembled structures are of interest (1). Filmless detectors have increased the throughput, eased storage problems, and reduced radiation exposure hazards while eliminating the costs and hazardous processing waste due to film-based x-ray systems. Most x-radiography systems use a point source and high resolution detector array such as an x-ray image intensifier coupled to camera tubes (2) or scintillators coupled to charge coupled devices (CCDs) (3). Due to the relatively large size of these detectors, they are difficult, if not impossible, to use for some in-situ appilications. There is clearly a need for an examination system utilizing compact, i.e., miniature, radiation detectors for areas having limited access.

When an examination system is employed within enclosures containing radioactive, volatile, flammable, or corrosive materials, or enclosures maintained at high temperatures, expensive efforts are required to mitigate these damaging environments before introducing the examination probe and/or x-ray source. There is clearly a need for an examination system utilizing environment-resistant components. There is also a need for an examination system in which the electrical components are remote from the hazardous area being examined to eliminate the possibility of an ignition of materials.

Hospitals today are switching to filmless radiography due to reduced budgets, strict radiation exposure policies, environmental concerns, and the need for convenient storage and fast transmission of information. By using detectors much more sensitive to x-rays than film, the dose received by a patient can be reduced by a factor of ten or even more (4). Also, by using purely electronic detectors the costs and hazardous waste due to film and its associated processing are eliminated. The electronic images generated can be stored in a much more compact manner and transmitted anywhere in the world in minutes. One of the main problems in the conversion to electronic imaging, however, is in trying to achieve the same spatial resolution as film. Some of the techniques currently used or under development are arrays of photodiode sensors coupled to phosphor screens (5), CCDs coupled to scintillators with a fiber optic taper (6), and x-ray image intensifiers coupled to camera tubes (7). Many of these systems suffer from cost and/or resolution and contrast sensitivity problems. They, along with film, are also prone to a degradation of resolution due to scattered x-rays from the patient, thus producing a "fuzzy" picture. There is a need for an examination system utilizing simple, inexpensive detectors to produce clear, nearly scatter free and high resolution real-time images for use in the medical and dental fields.

The present invention is an examination system and method, based on the Reverse Geometry x-Ray® (RGX®)* radiography technique, which has been optimized to solve the aforementioned problems. The reverse geometry x-radiography technique "reverses" the size and location of the x-ray source and detector of the conventional x-radiography technique. With the RGX® system the object to be examined is placed next to a large raster scanning x-ray tube anode with a "point" detector located anywhere from a few centimeters to a meter away (see FIG. 1). The x-rays are produced when a microfocused beam of electrons strikes the high Z target/window anode. Magnetic deflection coils sweep the electron beam in a raster pattern across the broad anode plate producing a moving point x-ray source. A computer correlates the positions of the x-ray beam to pixels on a cathode ray tube screen with the output of the detector at each point giving a transmitted x-ray intensity value to the pixel.

*Reverse Geometry X-ray® and RGX® are registered trademarks of Digiray Corporation, 2239 Omega Road, San Ramon, Calif. 94583.

Real time stereoscopic images can be obtained with the RGX® system due to its fast scanning rate (approximately 0.25 seconds for 512×512 pixels, approximately 1 second for 1024×1024 pixels) and ability to read two point detectors simultaneously. The current system has a resolution of greater than 7 lp/mm and a contrast sensitivity of about 0.2% for thin, low density specimens (8). The use of a single channel point detector as the imaging element allows the use of small detector probes which can be placed inside objects to produce images of one area without interference from another area as would occur if the x-rays traversed the whole object prior to detection. The remoteness and small size of the detector eliminates detection of scattered x-rays thus improving resolution and removing "fuzziness" from the image.

The references cited above and throughout the following specification are listed in Appendix I of the application; they are incorporated by reference herein. Additional publications which are incorporated by reference herein are listed in Appendix II.

SUMMARY OF THE INVENTION

Accordingly, it is an object of the present invention to provide an examination system and method which utilize a flexible, miniature radiation detector probe.

It is another object of the present invention to provide an examination system and method which utilize environment-resistant components.

It is yet another object of the present invention to provide a fire-safe examination system, i.e., having electrical components remote from the examination area.

It is yet a further object of the present invention to provide an examination system and method which utilize inexpensive, simple radiation detectors.

A final object of the present invention is to provide an examination system and method which utilize a fast and bright scintillator to produce clear, nearly scatter free, and high resolution real-time images.

The invention is an examination system and method which utilize ionizing radiation and a flexible, miniature radiation detector probe. The preferred embodiment comprises a radiation source, at least one flexible, miniature radiation detector probe positioned in appropriate proximity to the object to be examined and to the radiation source with the object located between the source and the probe, a photodetector device attachable to an end of the miniature radiation probe, and a control unit integrated with a display device connected to the photodetector device. The miniature radiation detector probe comprises a scintillation element, a flexible light guide having a first end optically coupled to the scintillation element and having a second end attachable to the photodetector device, and an opaque, environmentally-resistant sheath surrounding the flexible light guide. The miniature radiation probe may be portable and insertable, or may be fixed in place within the object to be examined. An enclosed, flexible, liquid light guide is also presented, which comprises a thin-walled flexible tube, a liquid contained within the tube, a scintillation element located at the first end of the tube, a closure located at the second end of the tube, and an opaque, environmentally-resistant sheath surrounding the flexible tube. Alternatively, the tube can have a closure at both ends and have a separate scintillation element.

BRIEF DESCRIPTION OF THE DRAWINGS

The above and numerous other objects of the invention that may be achieved by the method and preferred embodiment of the invention will be more readily understood from the following detailed description and the appended drawings wherein.

DESCRIPTION OF THE PREFERRED EMBODIMENT

Figure 1:
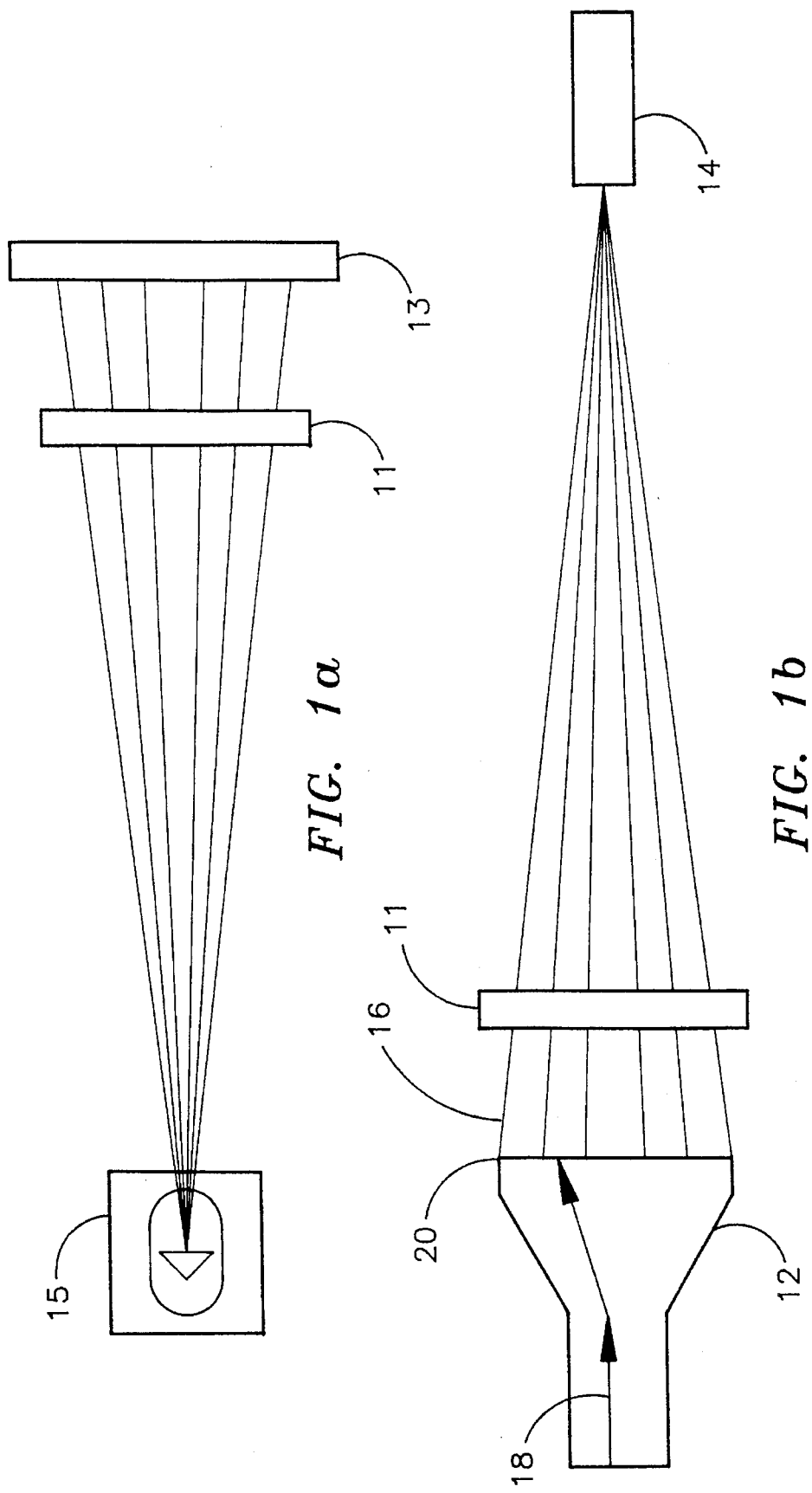
FIG. 1 compares the reverse geometry x-radiography technique with the conventional x-radiography technique.

The first portion of the following detailed description concerns the examination system of the present invention. The next portion concerns the flexible, liquid light guide of the present invention. The final portion of the description concerns the examination method of the present invention.

Referring now to the drawings in detail, wherein like reference characters indicate like parts throughout the several figures, reference numeral 10 refers to the examination system, reference numeral 12 refers to the radiation source, and reference numeral 14 refers to the flexible, miniature radiation detector probe.

Examination System

FIG. 1 compares the reverse geometry x-radiography technique with the conventional x-radiography technique. In conventional x-radiography, the object 11 to be examined is placed closer to the detector 13 than to the point x-ray source 15. In the ideal representation reverse geometry x-radiography reverses the size and location of the x-ray source 12 and detector 14 relative to the object 11 to be examined. The object 11 is placed next to a large raster scanning x-ray tube anode 12 with a point detector 14 located anywhere from a few centimeters to about a meter away. The x-rays 16 are produced when a microfocused beam of electrons 18 strikes the high Z target/window anode 20. Magnetic deflection coils (not shown) sweep the electron beam in a raster pattern across the broad anode plate producing a moving point x-ray source. A computer (not shown) correlates the positions of the x-ray beam 16 to pixels on a cathode ray tube screen (not shown) with the output of the detector at each point giving a transmitted x-ray intensity value to the pixel.

Figure 2:
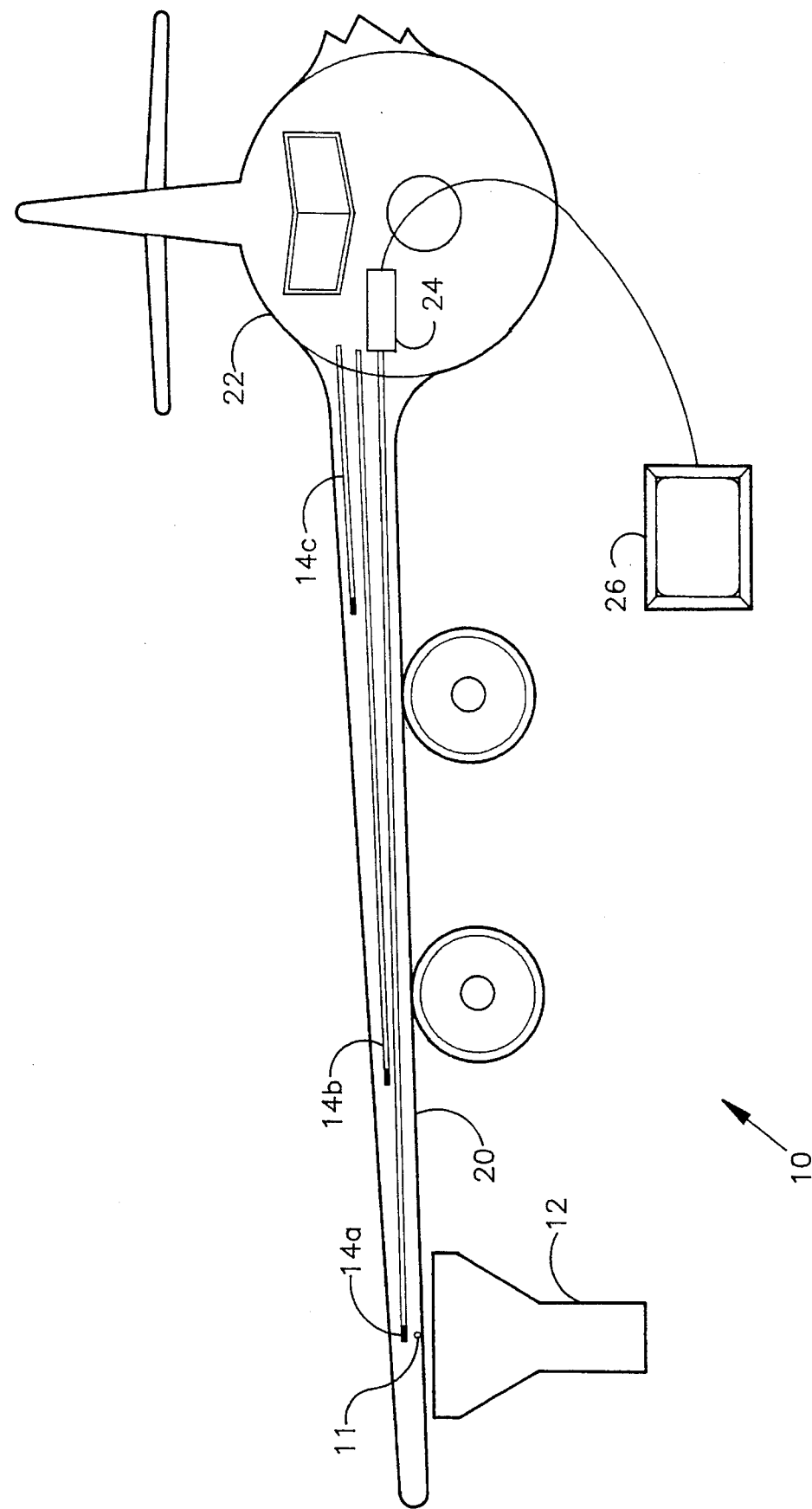
FIG. 2 is a schematic illustration of one of the applications of the examination system of the present invention.

FIG. 2 is a schematic illustration of one embodiment of the examination system of the present invention. Examination system 10 comprises a radiation source 12, at least one flexible, miniature radiation detector probe 14a, 14b, and 14c (three are shown) positioned inappropriate proximity to object 11 to be examined and to radiation source 12 with object 11 located between source 12 and probe 14a, a photodetector device 24 attachable to miniature radiation detector probe 14a, and a control unit integrated with a display device 26 connected to photodetector device 24. In FIG. 2 examination system 10 has been employed to inspect a wing 20 of airplane 22; threaded into wing 20 are three (3) flexible, miniature radiation detector probes 14a, 14b, and 14c.

Radiation source 12 is a large raster scanning x-ray tube anode, preferably the Digiray RGX® Reverse Geometry X-ray® System (Digiray Digital X-Ray Systems, San Ramon, Calif.). Photodetector device 24 is a photomultiplier tube (PMT), preferably a Hamamatsu R268 PMT (Hamamatsu Corporation, Middlesex, N.J.) or EMI 9268 PMT (Thorn EMI Electron Tubes Inc., Rockaway, N.J.). These two models are linear and stable enough to handle the extremes of the incoming signals if a special voltage divider, developed by CEBAF, is used to keep the supply voltage constant and to keep the last few dynodes from becoming saturated by increasing the voltage differences between them. The details of this modification are provided in CEBAF Detector Group Technical Note, Jun. 10, 1993 (9) which is incorporated herein by reference. The control unit is a computer, preferably an IBM PC compatible computer with an 80386 processor or higher, having a CRT monitor for displaying the images.

In an alternative embodiment (not shown) the flexible, miniature radiation detector probes are built into the object to be examined. For example, when an airplane is constructed, the miniature radiation detector probes are permanently installed; in composite aircraft construction they are laminated in the structure and a port exists on the plane which provides access to the ends of the flexible light guides of the probes. Alternatively, tubes for ducts are embedded either in the lamination of a composite structure or as part of the wing spar in a conventional metal structure. The flexible, miniature radiation detector probes are moved within the tubes or ducts to appropriate inspection positions.

Figure 3:
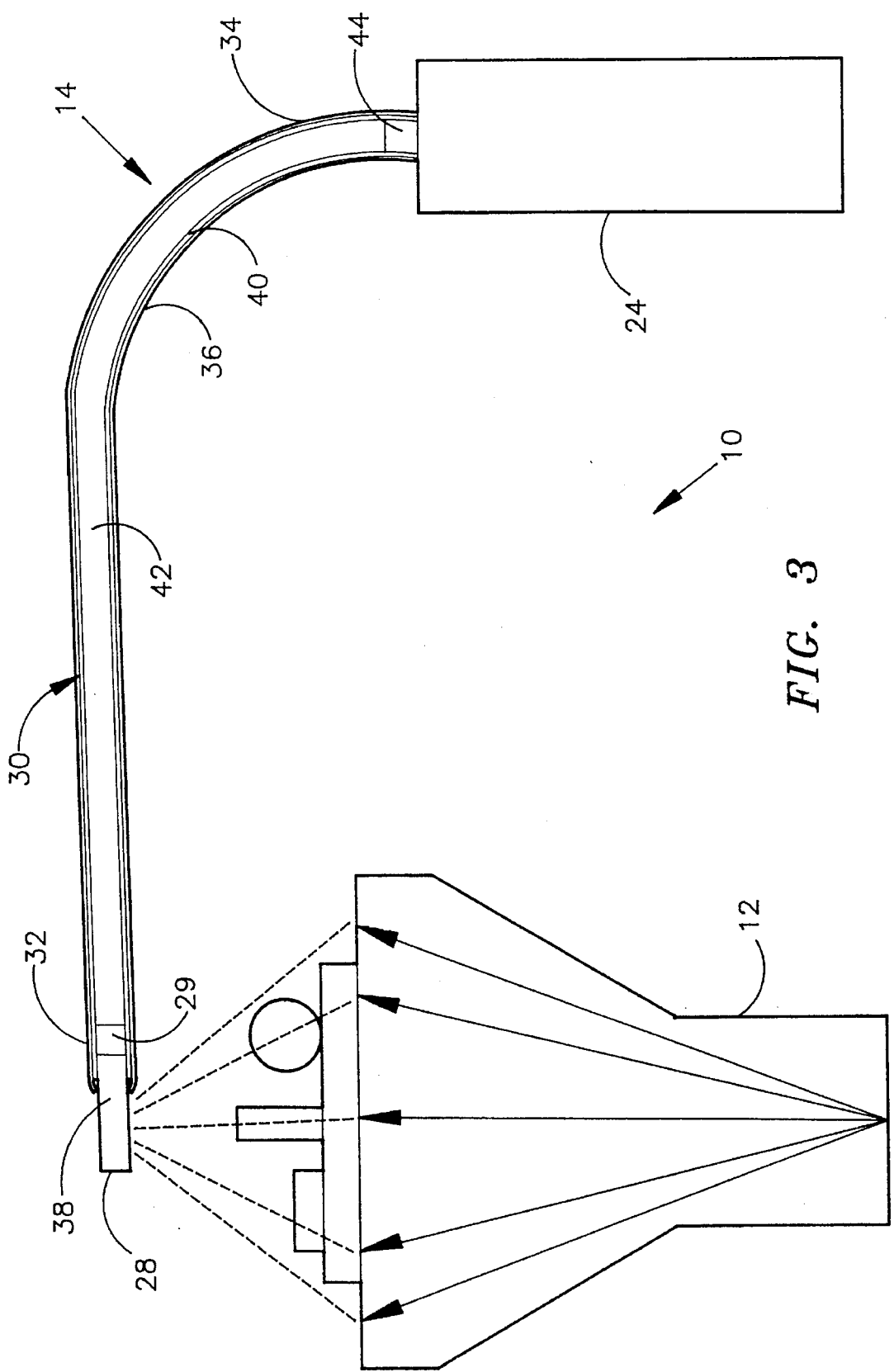
FIG. 3 is a schematic illustration of the flexible, miniature radiation detector probe of the examination system.

FIG. 3 is a schematic illustration of the flexible, miniature radiation detector probe 14 and photodetector device 24 of examination system 10. Miniature radiation detector probe 14 comprises a scintillation element 28, a flexible light guide 30 having a first end 32 optically coupled to scintillation element 28 and having a second end 34 attachable to photodetector device 24, and an opaque, environmentally-resistant sheath 36 surrounding light guide 30. Miniature radiation detector probe 14 is approximately 3–5 mm in diameter, and may be portable and insertable, or may be fixed in place within the object to be examined. However, for applications requiring a catheterizable radiation detector probe, i.e., within the human body, probe 14 is approximately 1 mm to approximately 3 mm in diameter. In other applications, probe 14 may be as large as 10 mm in diameter.

Scintillation element 28 comprises an inorganic material, preferably cerium-doped lutetium oxyorthosilicate (Schlumberger-Doll Research, Ridgefield, Conn.), which is typically 3 mm diameter×5 mm long. Other materials which may be used for scintillation element 28 include cerium-doped gadolinium orthosilicate (Marubeni Specialty Chemical, Inc., White Plains, N.Y.) and cerium fluoride: (Optovac, North Brookfield, Mass.). In addition, a polymer material, lead-doped polystyrene (Bicron Corporation, Newbury, Ohio), may also be used as a scintillator. These materials have a fast decay rate of no more than 50 nanoseconds and very low levels of afterglow. These characteristics of scintillation element 28 provide for the very high speed operation and high image quality of examination system 10. These materials have the additional characteristic of high stopping power for X-rays. Consequently, the intensity of radiation source 12 can be reduced by a factor of about 10–100, i.e., to approximately 0.2 mR/sec, compared to other radiation sources, Without affecting image quality in a major way. End 38 of scintillation element 28, which is typically polished and circular in shape, is optically coupled to flexible light guide 30.

Flexible light guide 30 has a first end 32 optically coupled to scintillation element 28 and a second end 34 attachable to photodetector device 24. Flexible light guide 30 may be as long as about ten meters or longer. An opaque, environmentally-resistant sheath 36 surrounds flexible light guide 30. Sheath 36 is made of a polymer material, preferably black polyethylene heat-shrink tubing (DuPont, Wilmington, Del.) having a wall approximately 0.25 mm thick, and serves two purposes: (1) it blocks ambient light from entering flexible light guide 30 and (2) it provides an abrasion and corrosion resistant surface.

Flexible Liquid Light Guide

Figure 4:
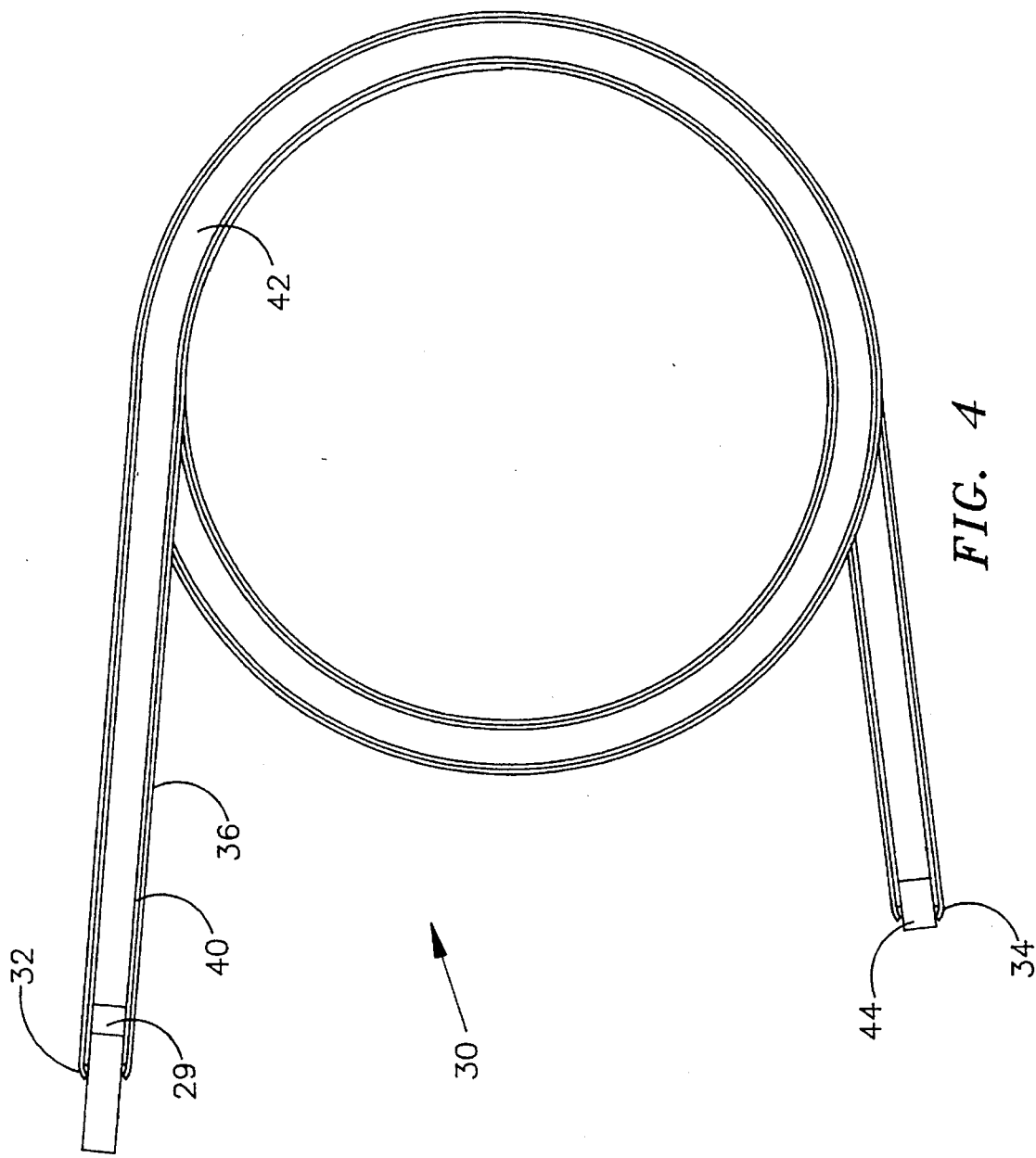
FIG. 4 is a schematic illustration of one embodiment of the flexible, liquid core light guide.

FIG. 4 is a schematic illustration of one embodiment of flexible light guide 30 which comprises a flexible tube 40, a liquid 42 contained within tube 40, a closure 29 located at a first end 32 of tube 40, a closure 44 located at a second end 34 of tube 40, and an opaque, environmentally-resistant sheath 36 surrounding tube 40. Flexible light guide 30 may be as long as about ten meters or longer, and may range from approximately 1 mm to approximately 10 mm in diameter, depending on the specific application. Flexible tube 40 is made of a polymer material, preferably fluorinated ethylene polypropylene (FEP) polytetrafluorethylene tubing (DuPont) having a thin wall approximately 0.01–0.04 inch thick. Liquid 42 within flexible light guide 30 is preferably a highly purified grade mineral oil such as highly transparent mineral oil provided by Bicron Corporation (Newbury, Ohio). Tube 40 has an index of refraction significantly lower than that of liquid 42 in order for flexible light guide 30 to efficiently transmit light. Closures 29 and 44 are made of a plastic material or other material transparent to the light being transmitted. Sheath 36 is made of a polymer material, preferably black polyethylene heat-shrink tubing (DuPont) having a wall approximately 0.25 mm thick, and serves two purposes: (1) it blocks ambient light from entering flexible light guide 30 and (2) it provides an abrasion and corrosion resistant surface. This embodiment may have application as a light transfer device in other types of systems.

Method for Examining Objects

A method for examining objects is presented, which comprises the following steps:

1. A radiation source, a flexible, miniature radiation detector probe, a photodetector device, a control unit integrated with a display device, and an object to be examined are provided.

2. The radiation source is positioned in appropriate proximity to the object to be examined.

3. The flexible, miniature radiation detector probe is positioned in appropriate proximity to the object to be examined and to the radiation source, with the object located between the the source and the probe.

4. The radiation emitted by the radiation source is directed at the object to be examined.

5. The radiation transmitted through the object being examined is detected with a scintillation element contained within the miniature radiation detector probe.

6. Photons emitted by the scintillation element are directed down a flexible light guide within the miniature radiation detector probe to a photodetector device.

7. Electrical signals generated by the photodetector device are sent to a control unit.

8. The electrical signals are correlated with the position of the radiation source using the control unit.

9. An image corresponding to the object being examined is displayed on the display device.

The system and method of the present invention have been used to detect a crack only 0.005 inch wide in a honeycombed type of aircraft wing structure (10,11). This is an example of the clear, nearly scatter free, high resolution images generated with the present invention.

The advantages of the present invention are numerous. First, because the examination system and method utilize a fast scintillator to produce clear, nearly scatter free, and high resolution real-time images, they have many applications in non-destructive material testing and in the medical and dental fields. Second, because the examination system and method utilize environment-resistant components and have electrical components remote from the examination area, they may be used to examine areas containing hazardous materials. Finally, because the examination system and method utilize inexpensive, simple radiation detectors, they provide an economic advantage over more expensive systems. Many variations will be apparent to those skilled in the art. It is therefore to be understood that, within the scope of the appended claims, the invention may be practiced other than as specifically described.

APPENDIX I

1. R. Halmshaw, Industrial Radiography Theory and Practice, Applied Science Publishers, Englewood, N.J., 1981.

2, 7. See for example: Phillips Photonics line of Plumbicon camera tubes.

3, 6. B. Allen, Application of CCDs to Digital X-Ray Mammography, 1994 Symposium on Radiation Measurements and Applications, May 16–19, 1994, The University of Michigan, Ann Arbor.

4. A. Breskin et al., Recent Developments in Secondary Emission Gaseous X-ray Imaging Detectors, preprint WIS-93/102/Oct.-PH, Weizmann Institute of Science, Rehovot, Israel, 1993, submitted to Nuclear Instruments and Methods in Physics Research A.

5. L. E. Antonum et. al., A High Resolution, High Frame Rate, Flat-Panel TFT Imager for Digital X-ray Fluoroscopy and Radiography, SPIE 1994 Medical Imaging Conference, Newport Beach, Calif., Feb. 13–15, 1994.

8. R. D. Albert et al., Aerospace Applications of X-Ray System Using Reverse Geometry, Materials Evaluation, September 1993.

9. S. Majewski et al., Linearity Studies of Photomultipliers and Voltage Dividers for the CLAS Calorimeter (Final Report), CEBAF Detector Group Technical Note, Jun. 10, 1993.

10. R. Wojcik et al., Development of X-Ray Mini-Probes for the Digiray RGX System, 1994 Symposium on Radiation Measurements and Applications, May 16–19, 1994, The University of Michigan, Ann Arbor.

11. R. Wojcik et al., Medical Imaging with Reverse Geometry X-Radiography, SPIE 1994 Medical Imaging Conference, Newport Beach, Calif., Feb. 13–15, 1994.

APPENDIX II

1. R. D. Albert, X-Ray Scanning Method and Apparatus, U.S. Pat. No. 3,949,229, Apr. 6, 1976.

2. R. D. Albert, Scanning X-Ray Spectrometry Method and Apparatus, U.S. Pat. No. 4,519,092, May 21, 1985.

3. R. D. Albert, Method and Apparatus for Scanning X-Ray Tomography, U.S. Pat. No. 4,730,350, Mar. 8, 1988.

4. L. A. Majewski et al., Study of a Flexible Liquid Light Guide, Nuclear Instruments and Methods in Physics Research A 337:628–631 (1994).

What is claimed as new and desired to be secured by Letters Patent of the United States is:

1. An x-ray examination system, comprising:
   a radiation source which is a large raster scanning x-ray tube anode;
   at least one flexible, elongated miniature radiation probe including a flexible light guide with said flexible light guide having a liquid light guide core within a plastic tube, with the index of refraction of said plastic tube being significantly lower than the index of refraction of said liquid;
   a scintillation element with a fast decay rate of no more than 50 nanoseconds at a first end of said flexible light guide for positioning in appropriate proximity to an object to be examined and to said radiation source with said scintillation element being of substantially the same width as the diameter of said liquid light guide core with the entire length of said light guide and scintillator being of substantially the same transverse dimension;
   a photodetector device attachable to a second end of said flexible light guide of said probe; and
   a control unit integrated with a display device connected to said photodetector device.

2. An examination system as recited in claim 1, wherein said liquid within said flexible light guide is selected from the group consisting of mineral oil and polysiloxane.

3. An examination system as recited in claim 1, wherein said flexible, miniature radiation probe includes an opaque, environmentally-resistant sheath surrounding said flexible light guide.

4. An examination system as recited in claim 1, wherein said scintillation element comprises an inorganic material.

5. An examination system as recited in claim 1, wherein said scintillation element comprises an inorganic material selected from the group consisting of cerium-doped lutetium oxyorthosilicate, cerium-doped gadolinium orthosilicate, and cerium fluoride.

6. An examination system as recited in claim 1, wherein said scintillation element comprises a polymer material.

7. An examination system as recited in claim 6, wherein said polymer material is selected from the group consisting of lead-doped polystyrene and polyvinyltoluene-based material.

8. A method for examining an object comprising the steps of:
   (a) (1) providing a radiation source which is a large raster scanning x-ray tube anode;
   (a) (2) providing at least one flexible, elongated miniature radiation probe including a flexible light guide with said flexible light guide having a liquid light guide core within a plastic tube, with the index of refraction of said plastic tube being significantly lower than the index of refraction of said liquid;
   (a) (3) providing a scintillation element with a fast decay rate of no more than 50 nanoseconds at a first end of said flexible light guide with said scintillation element being of substantially the same width as the diameter of said liquid light guide core with the entire length of said light guide and scintillator being of substantially the same transverse dimension;
   (a) (4) providing a photodetector device attachable to a second end of said flexible light guide of said probe;
   (a) (5) providing a control unit integrated with a display device connected to said photodetector device;
   (a) (6) providing an object to be examined;
   (b) positioning said radiation source in appropriate proximity to the object to be examined;
   (c) positioning said miniature radiation detector probe in appropriate proximity to the object to be examined and to said radiation source, with the object located between said source and said probe;
   (d) directing radiation emitted by said radiation source at the object to be examined;
   (e) detecting radiation transmitted through the object being examined with said scintillation element contained within said miniature radiation detector probe;
   (f) directing photons emitted by said scintillation element down said flexible light guide within said miniature radiation detector probe to said photodetector device;
   (g) sending electrical signals generated by said photodetector device to said control unit;
   (h) correlating said electrical signals with the position of said radiation source using said control unit; and
   (i) displaying an image corresponding to the object being examined on said display device.

* * * * *